US005798103A

United States Patent [19]

Mooi

[11] Patent Number: 5,798,103
[45] Date of Patent: Aug. 25, 1998

[54] WHOOPING COUGH VACCINE COMPRISING A FIMBRIA PROTEIN

[75] Inventor: Frederik Robert Mooi, Utrecht, Netherlands

[73] Assignee: De Staat der Nerderlanden Vertegenwoordigd Door de Minister Van Welzijn, Volksgezondheid en Cultuur, Rijswijk, Netherlands

[21] Appl. No.: 2,024

[22] Filed: Jan. 8, 1993

[30] Foreign Application Priority Data

Jan. 8, 1992 [EP] European Pat. Off. ............... 9220038

[51] Int. Cl.$^6$ ............... A61K 39/02; A61K 39/10; A61K 21/02
[52] U.S. Cl. ............... 424/240.1; 424/184.1; 424/185.1; 424/242.1; 424/253.1; 424/254.1; 530/350; 435/69.1; 435/69.3; 435/69.7; 435/71.1
[58] Field of Search ............... 424/92, 184.1, 424/240.1, 242.1, 253.1, 254.1, 185.1; 530/300, 350, 324, 326; 435/69.1, 69.3, 697, 71.1

[56] References Cited

U.S. PATENT DOCUMENTS 4,795,803 1/1989 Lindberg ............... 530/324

FOREIGN PATENT DOCUMENTS

WO85/05037 11/1985 WIPO ............... A61K 39/00

OTHER PUBLICATIONS

Locht et al The EMBO Journal 11:3175–3183, 1992.
Willems et al Molecular Microbiology 9: 623–634, 1993 Isolation of a Pututive Fimbrial Adhesiv from *Bordetelli pertussis* & the Identification of its Gene.

Weiss et al Ann. Review Microbiol 40: 661–86, 1980 Virulence Factors of *Bordetella Pertussis*.

Kimura et al Infect. & Immunity 58:7–16, 1990 *Bordetella pertussis* Filamentons Hemagglutinin: Evaluation as Protective Antigen & Colonization Factor in Mouse Respiratory Infection Model.

Mooi et al Microbial Pathogenesis 12:127–135, 1992.

Robinson et al Vaccine 3:11–22, 1985.

Novotry et al The Journal of Infect. Diseases 164:114–22, 1991.

"Microbial Pathogenesis", *Characterization of Fimbrial Subunits from Bordetella Species*, vol. 2, 1987, pp. 473–484 by Frits R. Mooi et al.

"Tokai Journal of Experimental Clinical Medicine", *Bordetella Pertussis Pilin and Pilin–Like Genes*, vol. 13, suppl. 1988, pp. 235–237 by F. de Ferra et al.

*Primary Examiner*—Hazel F. Sidberry
*Attorney, Agent, or Firm*—Young & Thompson

[57] ABSTRACT

The invention relates to acellular vaccines being effective against whooping cough and is based on a functional component of the fimbriae of *Bordetella pertussis* i.e. the actual adhesin molecule being a "minor" component in the fimbriae. The vaccines according to the invention have the advantage that both they may induce an effective immune respons against all *B. pertussis* strains and—most likely—also against *Bordetella paratertussis* being the second important causative agent of whooping cough. Further, the vaccines may also be used for veterinary applications, to protect against *Bordetella bronchiseptica* infections.

7 Claims, 8 Drawing Sheets

Fig-4

Peptide 6:

```
        325              320              325
         |                |                |
(K)  A  Q  Y  Y  Q  T  S  T  S  T  S  A  G
```

DNA probe derived from peptide 6:

```
     (K)   A    Q    Y    Y    Q    T
5'- AAG - GCC - CAG - TAC - TAC - CAG - ACC -3'
                      T     T
```

Peptide 16:

```
        295              300              305              310
         |                |                |                |
(K)  I  A  L  P  E  A  Q  Q  T  E  S  A  T  F  S  L  P  M  K
```

Peptide 19:

```
ATG AGC CAG ATA TTC GCT GAC CGC CGG GCC GCC GTG CCC GCG CGC GTA    48
Met Ser Gln Ile Phe Ala Asp Arg Arg Ala Ala Val Pro Ala Arg Val
        -35                 -30                 -25

ATT TCC TTC TGC GGG GCC GCG CTT GCC GTC TGG GCA GGC CTG GCC GTG    96
Ile Ser Phe Cys Gly Ala Ala Leu Ala Val Trp Ala Gly Leu Ala Val
    -20                 -15                 -10

CAG CCC GCC ATG GCC GTC GAT CCG CCG GTG GAC TGC GGC CGG GCG CTA   144
Gln Pro Ala Met Ala Val Asp Pro Pro Val Asp Cys Gly Arg Ala Leu
-5                   1                   5                  10

GGC TTG CAT TTC TGG TCG AGC GCC TCG CTC ATC TCC GAC CAG ACA CCC   192
Gly Leu His Phe Trp Ser Ser Ala Ser Leu Ile Ser Asp Gln Thr Pro
            15                  20                  25

GAT GGG ACG CTG ATC GGC AAG CCC GTG GTC GGG CGG TCC CTG CTG TCC   240
Asp Gly Thr Leu Ile Gly Lys Pro Val Val Gly Arg Ser Leu Leu Ser
        30                  35                  40

AAG AGC TGC AAG GTG CCG GAC GAC ATC AAG GAA GAC CTC AGC GAC AAC   288
Lys Ser Cys Lys Val Pro Asp Asp Ile Lys Glu Asp Leu Ser Asp Asn
    45                  50                  55

CAT GAC GGC GAA CCG GTC GAC ATC GTG CTG GAA CTG CTG GGC AGT AAC TAC   336
His Asp Gly Glu Pro Val Asp Ile Val Leu Glu Leu Leu Gly Ser Asn Tyr
60                  65                  70                  75
```

Fig-5 (2)

```
AAG ATC CGG CCG CAG TCC TAT GGC CAT CCG GGC ATC GTG GAC TTG          384
Lys Ile Arg Pro Gln Ser Tyr Gly His Pro Gly Ile Val Asp Leu
                80          85          90

CCG TTC GGC TCC ACG GAG GAG ACC GGC ATC TAT ATC GCC GAT TTC          432
Pro Phe Gly Ser Thr Glu Glu Thr Gly Tyr Ile Ala Ile Asp Phe
            95          100         105

GGC AGT TCG CCG ATG CAG AAG GTC GGC GAA CGG CAG TGG CTG TAT CCC      480
Gly Ser Ser Pro Met Gln Lys Val Gly Glu Arg Gln Trp Leu Tyr Pro
        110         115         120

CAG AAA GGC GAA GTG CTT TTC GAC GTG CTC ACC ATC AAC GGC GAC AAC      528
Gln Lys Gly Glu Val Leu Phe Asp Val Leu Thr Ile Asn Gly Asp Asn
    125         130         135

GCG GAG GTT CGC TAT CAG GCG ATC AAG GTC GGG CCA CTC AAG CGG CCG      576
Ala Glu Val Arg Tyr Gln Ala Ile Lys Val Gly Pro Leu Lys Arg Pro
140         145         150         155

CGC AAG CTG GTG CTG TCG CAG TTT CCG AAC CTG TTC ACC TAC AAG TGG      623
Arg Lys Leu Val Leu Ser Gln Phe Pro Asn Leu Phe Thr Tyr Lys Trp
        160         165         170
```

Fig-5 (3)

```
GTT TTC ATG CGC GGG ACC AGC CAG GAG CGC GTG CTG GCG CAG GGG ACC    672
Val Phe Met Arg Gly Thr Ser Gln Glu Arg Val Leu Ala Gln Gly Thr
            175                 180                 185

ATC GAC ACC GAC GTC GCC ACC AGC ACC ATC GAC CTG AAA ACC TGC CGC    720
Ile Asp Thr Asp Val Ala Thr Ser Thr Ile Asp Leu Lys Thr Cys Arg
            190                 195                 200

TAT ACC TCG CAG ACG GTC AGC CTG CCC ATC ATC CAG CGT TCC GCG TTG    768
Tyr Thr Ser Gln Thr Val Ser Leu Pro Ile Ile Gln Arg Ser Ala Leu
            205                 210                 215

ACC GGC GTC GGT ACC ACC CTG ACC GAT TTC CAG ATG CCG TTC             816
Thr Gly Val Gly Thr Thr Leu Thr Asp Phe Gln Met Pro Phe
            220                 225                 230        235

TGG TGC TAT GGC TGG CCA AAG GTA TCG GTG TAC ATG AGC GCG ACG AAG    864
Trp Cys Tyr Gly Trp Pro Lys Val Ser Val Tyr Met Ser Ala Thr Lys
            240                 245                 250

ACG CAG ACC GGC GTA GAC GGC GTG GCG TTG CCG GCG ACC GGC CAG GCG    912
Thr Gln Thr Gly Val Asp Gly Val Ala Leu Pro Ala Thr Gly Gln Ala
            255                 260                 265
```

Fig-5(4)

```
GCC GGC ATG GCC AGC GGC GTA GGC GTC CAG TTG ATC AAC GGC AAG ACG   960
Ala Gly Met Ala Ser Gly Val Gly Val Gln Leu Ile Asn Gly Lys Thr
            270                 275                 280

CAG CAG CCG GTC AAG CTG GGC CTG CAG GGC ATC GCC TTG CCC GAG      1008
Gln Gln Pro Val Lys Leu Gly Leu Gln Gly Ile Ala Leu Pro Glu
        285                 290                 295

GCG CAG ACT GAG TCG GCG ACG TTC TCG CTG CCC ATG AAG GCG CAG      1056
Ala Gln Thr Glu Ser Ala Thr Phe Ser Leu Pro Met Lys Ala Gln
    300                 305                 310             315

TAC TAC CAG ACC TCC ACT TCA ACC TCG GCG AAG CTG TCC GTC ACC      1104
Tyr Tyr Gln Thr Ser Thr Ser Thr Ser Ala Gly Lys Leu Ser Val Thr
                320                 325                 330

TAC GCC GTG ACC TTG AAC TAT GAC TGA CGC AAC GAA CCG TTT CCG GCC GGG 1155
Tyr Ala Val Thr Leu Asn Tyr Asp ---
335
```

Fig-6

ATC-GAG-GGA-AGG-ATT-TCA-GAA-TTC-GGA-TCC-GTC-GAT-CCG-//-TAT-GAC-TAG-......
ile glu gly arg ile ser glu phe gly ser val asp pro // tyr asp stop BamHI

WHOOPING COUGH VACCINE COMPRISING A FIMBRIA PROTEIN

BACKGROUND OF THE INVENTION

1. Field of the Invention

The invention relates to a whooping cough vaccine.

2. Description of the Related Art

Whooping cough or pertussis is caused by two closely related bacteria, *Bordetella pertussis* and *Bordetella parapertussis* [Preston N. W. (1988). Pertussis Today. In:Pathogenesis and Immunity in Pertussis (Eds. Wardlaw A. C., and Parton R.). John Wiley and Sons, 1–18]. *B. pertussis* is most frequently isolated from whooping cough patients (in 70 to 97% of the cases), so most research is focused on this organism. *B. pertussis* attaches to the ciliated cells of the respiratory tract, where it proliferates and produces a number of toxins. Locally, the infection results in destruction of the ciliated cells, which can result in obstruction of the respiratory tract, paroxysmal cough, apnoea and encephalopathy, sometimes accompanied by fever. Whooping cough can occur in any age group, however, morbidity is highest in the age group below 2 years.

Although *B. pertussis* is sensitive for a number of antibiotics, treatment with antibiotics is generally not effective after whooping cough has been diagnosed, presumably because toxins produced by the bacteria have already damaged the respiratory tract. Thus prevention of whooping cough by means of vaccination is highly desirable.

At present, vaccination is performed with a so-called whole-cell vaccine, which is composed of whole, killed, *B. pertussis* bacteria. The whole-cell vaccine is able to induce protection against whooping cough. However, a disadvantage of such a whole-cell vaccine is its ill definition and the presence of many non-functional components, some of which are toxic. Indeed, it has been observed that the whole-cell vaccine causes local and systemic side effects [Ross, E. M. (1988). Reactions to whole-cell pertussis vaccine. In:Pathogenesis and Immunity in Pertussis (Eds. Wardlaw A. C., and Parton R.). John Wiley and Sons, 275–398].

Because of the adverse side effects caused by the whole-cell vaccine, research is being performed to develop an acellular whooping cough vaccine. Ideally, this type of vaccine will contain only those components, which are nontoxic and required to induce protective immunity. Bacterial components which are being considered for the acellular whooping cough vaccine include, outer membrane proteins, inactivated toxins, and adhesins. Adhesins are bacterial factors which allow the bacteria to attach to host tissues. This attachment is a first and crucial step in the development of an infection. Since antibodies against adhesins may stop the infection in an early phase, adhesins are considered potential vaccine components.

An important group of bacterial adhesins is formed by fimbriae. Fimbriae are extracellular filamentous proteins, composed of major and minor subunits. The major subunit constitutes the building block of the fimbria, whereas the minor subunits are present in small amounts in the fimbrial structure. Generally, one of the minor subunits contains the receptor binding site [De Graaf, F. K. (1990). Genetics of adhesive fimbriae of intestinal *Escherichia coli*. Curr. Topics Microb. Immunol. 151:29–53].

*B. pertussis* fimbriae are part of a number of experimental acellular vaccines [Robinson, A., and Ashworth L. A., (1988). Acellular and defined-component vaccines against pertussis. In: Pathogenesis and Immunity in Pertussis (Eds. Wardlaw A. C., and Parton R.), John Wiley and Sons, 399–417]. *B. pertussis* produces two antigenically distinct fimbriae, designated serotype 2 and 3 fimbriae. Epidemiological data [Griffith, E. (1998). Efficacy of whole-cell pertussis vaccine. In:Pathogenesis and Immunity in Pertussis (Eds. Wardlaw A. C., and Parton R. John Wiley and Sons, 353–374], and studies performed in animal models [Robinson, A., Gorringe, A. R., Funnel, S. G. P., and Fernandez, M. (1989) Serospecific protection of mice against intranasal infection with *Bordetella pertussis*, Vaccine 7, 321–324] have indicated that fimbriae induce protective, but unfortunately serospecific immunity. There are some problems associated with the use of serotype 2 and 3 fimbriae in an acellular vaccine:

1. It is shown [see for instance Mooi F. R. et al. (1987), Characterization of fimbrial subunits from *Bordetella* species. Microbial Pathogenesis 2, 473–484 and Pedroni P. et al (1988), Cloning of a novel pilin like gene from *Bordetella pertussis*: homology to the fim2 gene. Molecular Microbiology 2, 539–543] that *B. pertussis* has the potential to produce at least one additional fimbrial serotype (serotype "X"). Thus, acellular vaccines should contain at least three fimbrial serotypes.

2. Fimbriae produced by *B. parapertussis*, the other causative agent of whooping cough, show very little antigenic relationship with *B. pertussis* fimbriae [Mooi et al., 1987, loc.cit.]. Therefore, it is unlikely that *B. pertussis* fimbriae will induce protection against *B. parapertussis* infections.

SUMMARY OF THE INVENTION

In view of the disadvantages attached to the known acellular vaccines against whooping cough Applicant has developed a vaccine against whooping cough based on the functional component of the fimbriae of *Bordetella pertussis* i.e. on the actual adhesin molecule being a "minor" component in the fimbriae. Up to now this adhesin molecule appears to be identical in different *B. pertussis* strains and vaccines based thereon induce an effective immune response against *B. pertussis*, irrespective of its fimbrial serotype. A further advantage of the vaccines according to the invention is lain in its presumptive use against *B. parapertussi*, irrespective of the fimbrial serotype carried by these bacteria.

Therefore the invention relates to the DNA sequence of the gene (designated fimD) coding for the adhesin molecule of *B. pertussis* fimbriae (designated FimD) or part of this sequence, vectors containing fimD or parts of fimD, microorganisms containing these vectors, the amino acid sequence of its gene product (FimD), peptides derived from FimD and vaccines against whooping cough based on FimD, or peptides derived thereof.

The use of FimD in an acellular whooping cough vaccine according to the invention does lead to the following improvements concerning whooping cough vaccines:

1. A simplification of the vaccine formulation. Two or more components (serotype 2, 3 and X fimbriae) are replaced by a single one (FimD).

2. The vaccine may protect not only against all *B. pertussis* serotypes, but also against *B. parapertusis* serotypes. FimD may even induce protection against veterinary diseases caused by *B. bronchiseptica*.

3. Antibodies are primarily induced against the functional component of the fimbria as such i.e. the adhesin molecule, leading to a more effective inhibition of adherence of the causative agents of whooping cough.

BRIEF DESCRIPTION OF THE DRAWINGS

Lane 1, starting material, pellet after centrifugation;

lane 2, starting material, supernatant after centrifugation lane 3, supernatant after treatment with SB14;

lane 4, pellet after SDS treatment;

lane 5, supernatant after SDS treatment;

lane 6, molecular weight standards (in kDa).

FimD, the 38 kDa outer membrane protein, and the major fimbrial subunits are indicated.

FIG. 6: DNA and predicted amino acid sequence of the region where the malE and fimD sequences were fused; SEQ ID NOS. 9 and 10. The fimD sequences are underlined, and the BamHI site used to Join the two sequences has been indicated.

DETAILED DESCRIPTION OF THE INVENTION (A) Isolation of FimD, generation of peptides, and N-terminal sequencing Highly purified fimbriae preparations from the *B. pertussis* strain Wellcome 28 (Robinson, A., c.s. (1989) Serospecific protection of mice against intranasal infection with *Bordetella pertussis*. Vaccine 7, 321–324) contain the serotype 2 and 3 major fimbrial subunits, and small amounts of additional polypeptides (FIG. 1, lane 1). One of these polypeptides was recognized by a monoclonal antibody (Poolman, J. T., c.s. (1990) Description of a Hybridoma Bank Towards Bordetella-Pertussis Toxin and Surface Antigens. Microbial Pathogenesis 8(6), 377–382) specific for the 38 Kda outer membrane protein of *B. pertussis* . A slightly larger polypeptide, tentatively designated FimD, was presumed to be a minor fimbrial subunit and was purified by detergent extraction and differential centrifugation (FIG. 1).

For the determination of the N-terminal sequence of FimD, the purified protein was subjected to SDS-polyacrylamide gel electrophoresis, and transferred to a PVDF Transfer Membrane (Millipore, PO Box 166, 4870 AD Etten-Leur, Holland). The part of the membrane containing FimD was cut out, and used for N-terminal amino acid sequence analysis. The determined N-terminal amino acid sequence is shown in FIG. 2. (SEQ ID NO. 1)

The N-terminal sequence of a number of internal FimD peptides was also determined. FimD was cleaved with a lysine-specific endopepti-dase, and the resulting peptides were separated by HPLC (FIG. 3). Three peptides were sequenced (FIG. 4). (SEQ ID NOS. 2, 5 and 6).

(B) Cloning and sequencing of the fimD gene

An oligonucleotide probe (SEQ ID NO. 3) was derived from one of the FimD peptides (peptide 6, FIG. 4) (SEQ ID NO. 2) and used to identify fimD sequences in a genomic bank of *B. pertussis* contained in EMBL3 (Mooi, F. R., van der Heide, H. G. J. c.s., (1987) Characterization of fimbrial subunits from Bordetella species. Microbial Pathogenesis 2, 473–484). A number of positive phages were detected, and one (designated λRIP500) was selected for further study. It appeared that a 8.5 kilobase SmaI fragment contained in λRIP500 hybridized to the oligonucleotide, suggesting that this DNA fragment harboured fimD. The 8.5 kilobase SmaI fragment was cloned into pUC19, and the resulting plasmid (pRIP504) was used for DNA sequencing. The fimD gene could be identified unambiguously on the basis of the oligonucleotide probe and the FimD peptides. The DNA sequence of fimD revealed that it codes for a precursor of FimD containing a signal peptide of 37 amino acid residues. The signal peptide is removed during or after transport of the precursor across the cytoplasmic membrane. The DNA sequence of fimD, and the deduced amino acid sequence of its product are shown in FIG. 5 (SEQ ID NOS 7 and 8).

(C) Construction and isolation of a MBP-FimD fusion protein

The FimD protein is produced in very low amounts by *B. pertussis*. Therefore, to facilitate the isolation of large amounts of FimD, the fimD gene was fused to a copy of the malE gene from which the region coding for the signal peptide was deleted. The malE gene codes for the maltose binding protein (MBP). To construct the fusion, the vector pMAL-cRI was used in which expression of the malE gene is controlled by the $P_{tac}$ promoter. In addition to the malE gene and the $P_{tac}$ promoter, pMAL-cRI contains the lacI gene, which codes for the repressor of the $P_{tac}$ promoter and keeps the expression from $P_{tac}$ low in the absence of inducer. When an inducer is added (for example IPTG), the repressor is inactivated, and high levels of transcription is initiated from $P_{tac}$ resulting in the production of large amounts of MBP, or MBP-fusion protein. The region containing the fusion between malE and fimD sequences is shown in FIG. 6 (SEQ ID NO. 9). Since MBP has affinity for maltose, MBP or MBP-fusion proteins can be purified by means of affinity column chromatography using a maltose column (Materials and Methods).

(D) Immunization of mice with a MBP-FimD fusion protein, and determining protective immunity MBP-FimD, MBP and PBS (phosphate buffered saline), were used to immunize mice. Two weeks after immunization, mice were challenged with the *B. pertussis* strain Tohama (B44). Directly following the challenge, and three and seven days thereafter, mice were sacrificed, and the amount of bacteria present in the nasopharynx, trachea and lungs was determined (Table 2). Significant protection, defined as a significant decrease in the colonization of mice immunized with MBP-FimD, compared to mice immunized with MBP or PBS, was observed on day 0, 3 and 7 in the trachea and lungs. No effect of immunization with MBP-FimD was observed in the nasopharynx. Protection in the nasopharynx probably requires a secretory IgA response, and the immunization route was not favourable for this type of immune response. Thus FimD sequences confer protective immunity in the lungs and trachea of mice.

MATERIALS AND METHODS

Strains and vectors

Strains and vectors used are indicated in Table 1 Bordetella strains ( see references cited in Table 1) were grown on Bordet-Gengou agar [Kendrick et al., (1970) Whooping cough. In: HL Bodely, EL Updyke, JO Mason, eds. Diagnostic procedures for bacterial, mycotic and parasitic infections, 5th edn. New York; American Public Health Association,: 106–117] or in Verwey medium [Verwey W. F., c.s. (1949), A simplified liquid culture medium for growth of *Haemophilus pertussis*, J. Bacteriol 50, 127–134]. *E. coli* strains were grown in NZ medium (per liter; 10 g NZ-amine A, 5 g NaCl, 1 g casamino acids, 5 g yeast extract, 2 g $MgSO_4.7H_2O$, pH 7.5) or on NZ agar plates (NZ medium supplemented with 1.5% agar). *E. coli* strains producing MBP or MBP-FimD were grown in Terrific broth, or on Terrific agar plates (Terrific broth supplemented with 1.5% agar).

TABLE 1

Strains and vectors used in this application

| Strains or vector | Relevant properties | Source or reference |
|---|---|---|
| *E. coli* strains: | | |
| DH5α | | 1 |
| BL21 | | 2 |
| *B. pertussis* strains: | | |
| Wellcome 28 | produces serotype 2 and 3 fimbriae | 3 |
| Tohama (B44) | challenge strain | 4 |
| Vectors: | | |
| EMBL3 | | 5 |
| pUC19 | | 6 |
| pUCBM21 | | 7 |
| pMAL-cRI | | 8 |
| pRIP504 | contains a copy of fimD (8.5 kilobase SMaI fragment in pUC19) | This work |
| pRIP640 | contains PCR fragment of fimD in polylinker | This work |
| pRIP642 | contains malE-fimD fusion | This work |

Figure 1:
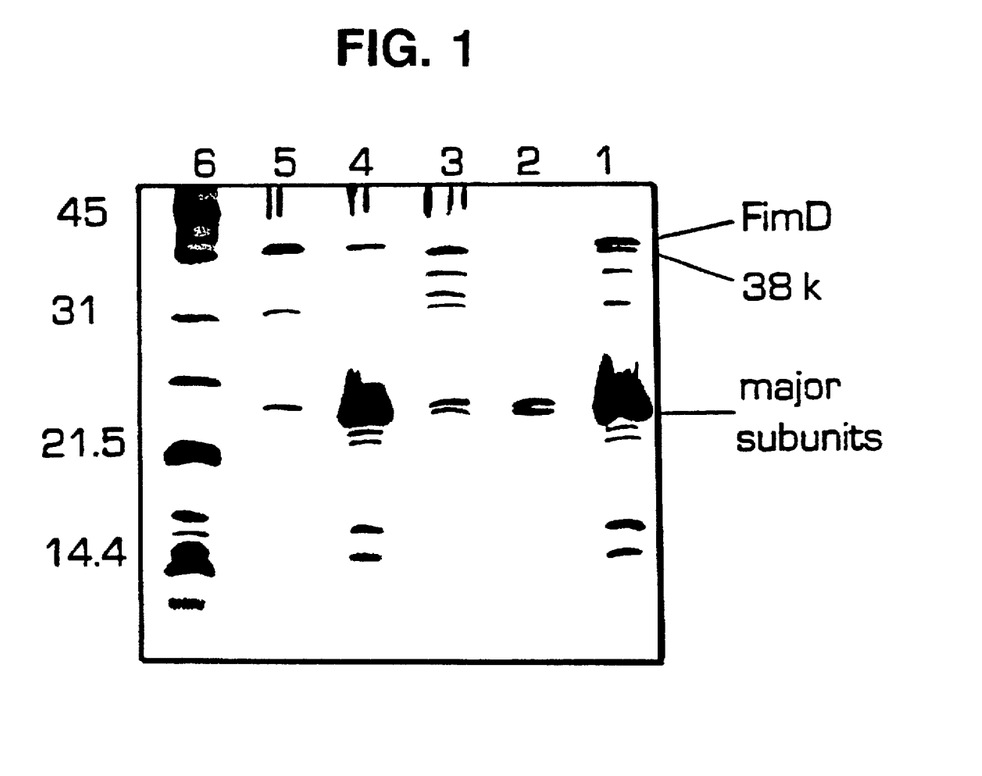
FIG. 1: Purification of FimD. Samples derived from various purification steps were subjected to SDS-polyacrylamide gel electrophoresis.
Figure 2:
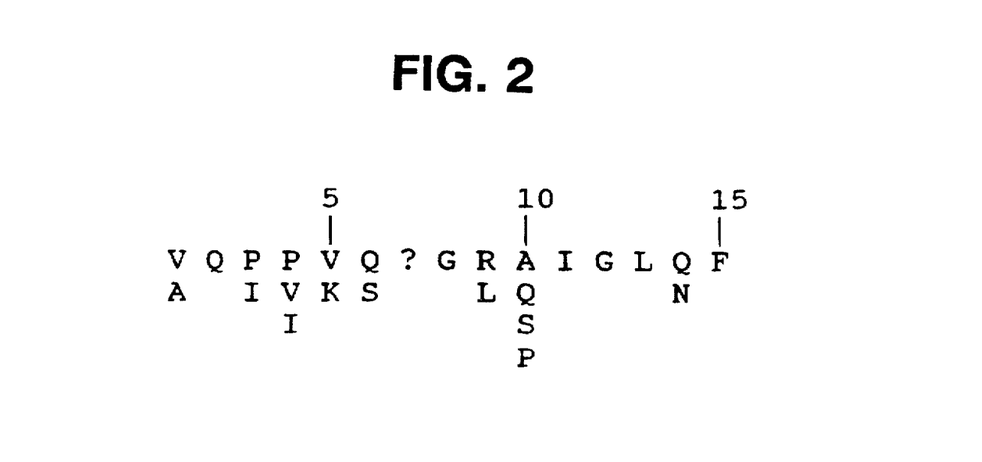
FIG. 2: SEQ ID NO.1 N-terminal amino acid sequence of FimD. At some positions, several amino acids were detected. The numbers refer to positions in the sequence of FimD.

1. GIBCO/BRL, Gaithersburg, Maryland 20877, USA
2. Novagen, Madison, WI, USA
3. Robinson, A., Gorringe, A. R., Funnel, S. G. P., and Fernandez M. (1989) Serospecific protection of mice against intranasal infection with *Bordetella pertussis*. Vaccine 7, 321–324.
4. Relman D. A., Dominighini M., Tuomanen E., Rappuoli R., and Falkow S. (1989), Filamentous hemagglutinin of *Bordetella pertussis*: nucleotide sequence and crucial role in adherence. Proc. Natl. Acad. Sci. USA 86, 2637–2641.
5. Karn, J., Brenner, S., and Barnett, L., (1983). New bacteriophage lambda vectors with positive selection for cloned inserts. In: R. Wu, L. Grossman, and K. Moldave, eds. Methods in Enzymology: Recombinant DNA, New York, Academic Press 101; 3–19.
6. Yanisch-Perron, C., Vieira, J., and Messing, J. (1985) Gene 33, 103.
7. Boehringer Mannheim, GmbH, Mannheim, Germany
8. New England Biolabs, Beverly MA, USA Isolation of FimD Fimbriae were purified from the Wellcome 28 strain by means of homogenization in a Silverson homogenizer, as described by Robinson et al., (1989) loc.git. Purified fimbriae (750 µg/ml) were dialysed against 20 mM Tris-HCl pH 8.0, and sedimented by centrifugation for 16 h at 4° C. and 200,000×g (FIG. 1; lane 1, pellet; lane 2, supernatant). The resulting pellet, mainly composed of fimbriae, was suspended in 20 mM Tris-HCl pH 8.0, and SB-14 (N-tetradecyl-N,N dimethylammonio-3-propane-sulfonate (SERVA, cat.no.35867)) was added to an end concentration of 1.5% (w/v). The suspension was incubated at 60° C. for 70 minutes, and subsequently subjected to centrifugation for 16 h at 16° C. and 200,000×g. The supernatant contained mainly outer membrane proteins, like the 38 kDa protein (FIG. 1, lane 3). The pellet was suspended in 20 mM Tris-HCl pH 8.0, and SDS (sodium dodecylsulphate) was added to an end concentration of 2% (w/v). Subsequently, the suspension was incubated for 60 min. at 60° C., after which it was subjected to centrifugation for 16 h at 16° C. and 200,000×g. The resulting pellet was mainly composed of the major fimbrial subunits (FIG. 1, lane 4), while the supernatant contained highly purified FimD (FIG. 1 lane 5). FimD was precipitated from the supernatant by the addition of 4 volumes of acetone. After incubating for 2 h on dry ice, the precipitate was collected by centrifugation for 90 min at 25° C. and 12,000×g. The resulting pellet was suspended in 25 mM Tris-HCl pH 8.5, 1 mM EDTA, 0.1% SDS. To 30 µl of this suspension, which contained approximately 6 µg FimD, 500 ng lyc-C (endoproteinase Lys-C, Boehringer, cat.no. 1047825) in 5 µl was added, and the suspension was incubated for 16 h at 35° C. The resulting peptides were purified by means of reversed-phase HPLC under the following conditions:

column: ODS2 (C18), narrow bore (2 mm)

gradient: 0–60% Acetonitrile in 60 min.

Figure 3:
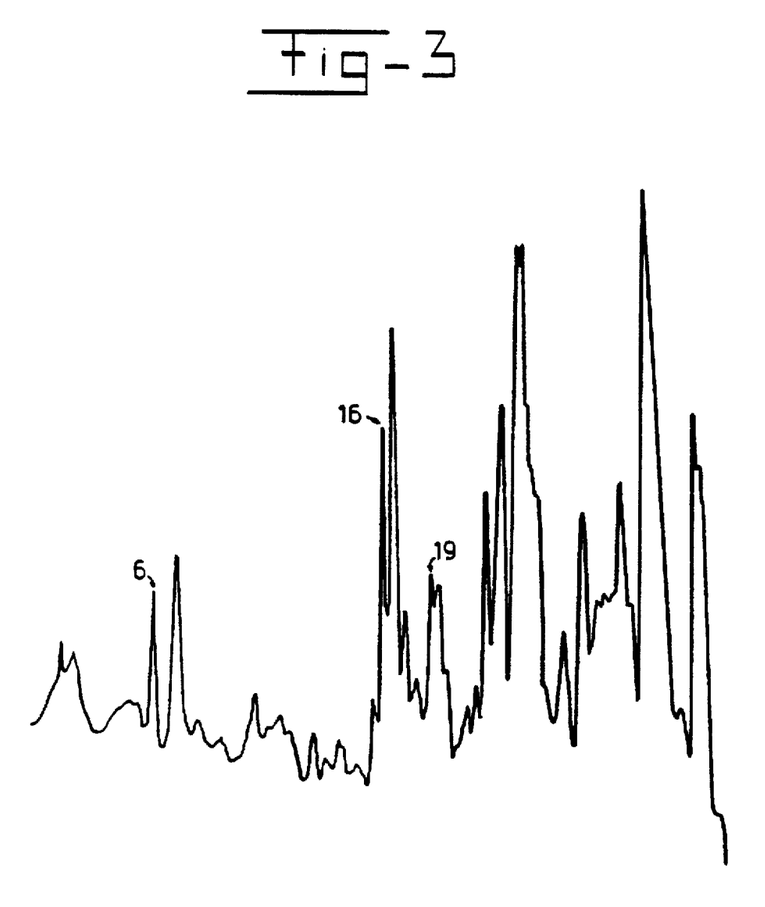
FIG. 3: Purification of peptides derived from FimD. FimD was treated with the lysine-specific endopeptidase lys-c, and the resulting peptides were separated with reversed-phase HPLC. Peaks 6, 16 and 19 (which eluted at 17, 29.5 and 31.5% acetonitrile, respectively) were used for amino acid sequencing.

Peaks 6, 16 and 19 (FIG. 3) were used for N-terminal amino acid analysis using an Applied Biosystems Model 470A Gas Phase Sequencer. Construction of a genomic bank of *B. pertussis* strain Tohama A genomic bank of the Tohama strain was constructed as described in Mooi et al., (1987) loc.cit. Briefly, chromosomal DNA was partially cleaved with Sau3AI, and fragments having sizes between 10 and 20 kilobases were isolated by preparative gel electrophoresis. The fragments were cloned into the BamHI site of EMBL3, and after in vitro packaging and transduction into *E. coli*, about 120,000 independent clones were obtained. The genomic bank was maintained in 20% glycerol at −70° C.

Identification of fimD sequences in the genomic bank

Figure 4:
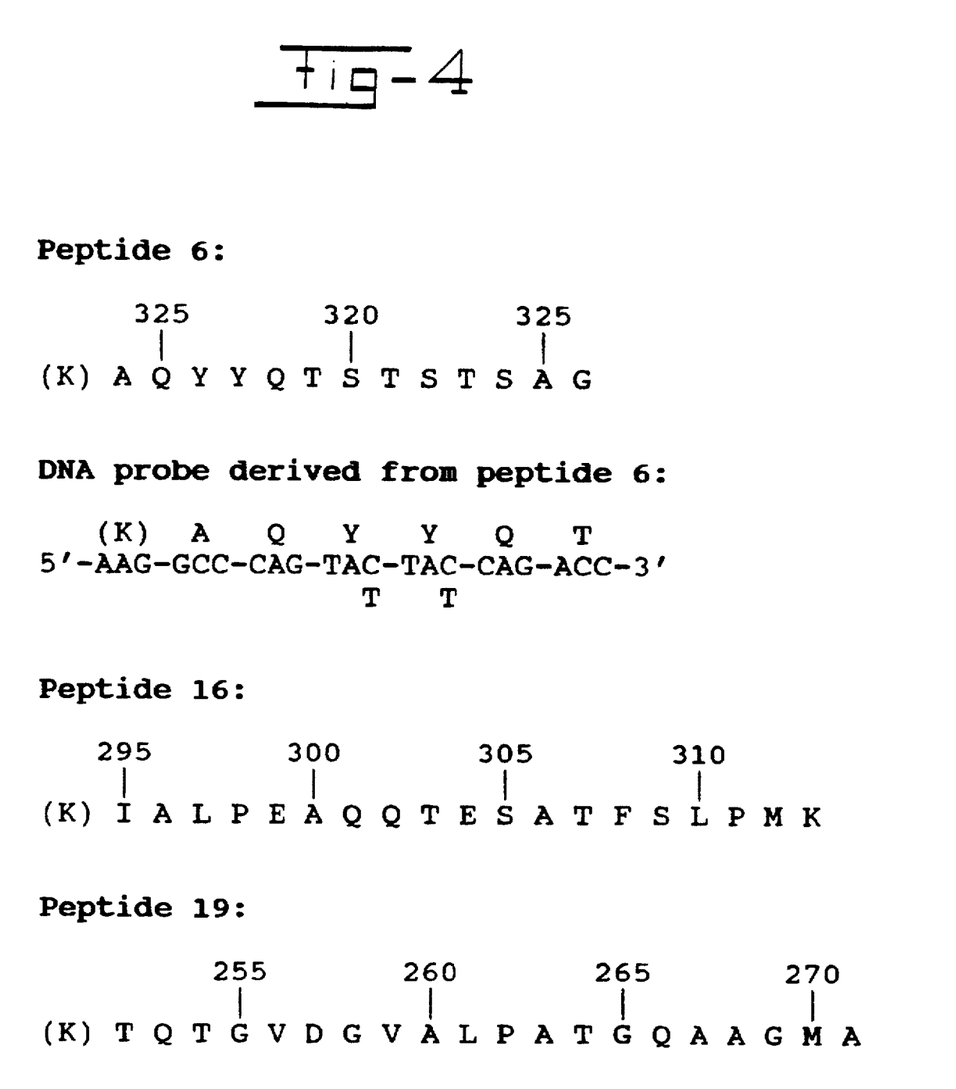
FIG. 4: N-terminal amino acid sequences of internal peptides derived from FimD; SEQ ID NO. 2, 5 and 6. The K residues between brackets were inferred from the specificity of the endopeptidase used to generate the peptides. The numbers refer to positions in the sequence of FimD. The oligo-nucleotide probe, derived from peptide 6; SEQ ID NO. 3, was used to identify DNA fragments harbouring fimD. The probe consists of a pool of four different oligonucleotides harbouring either a C or T at the wobble position of the fourth and fifth codon.

The genomic bank was screened for fimD sequences with an oligonucleotide (SEQ ID NO. 3) derived from peptide 6 (FIG. 4) (SEQ ID No.2). Plaques were transferred to Gene-Screen-Plus membranes (Du Pont, Boston, Mass., U.S.A.), and hybridized to the $^{32}$p-labeled oligonucleotide probe according to the instructions provided by Du Pont. Positive plaques were identified after autoradiography.

DNA techniques

Unless otherwise stated, DNA techniques were performed as described in by Sambrook et al., (1989), Molecular cloning: a laboratory manual; Second Ed., Cold Spring Harbor Laboratory Press.

Determining the DNA sequence of fimD

The DNA sequence of the DNA region containing fimD was determined on both strands using an ABI DNA sequencer (Applied Biosystems, Foster City, Calif., U.S.A.) following the protocols provided by the manufacturer. Overlapping fragments were generated using the Erase-a-Base System from Promega (Promega, 2800 Woods Hollow Road, Madison, Wis., U.S.A.). Fragments harbouring fimD sequences were identified by hybridization with the oligonucleotide (SEQ ID No.3) derived from peptide 6 (FIG. 4) (SEQ ID NO. 2).

Construction of a MBP-FimD fusion protein

The fimD gene was amplified from pRIP504 using the polymerase chain reaction (PCR) and the following primers:

5'-(ATGGATCC)-GTC-GAT-CCG-CCG-GTG-G-3' (SEQ ID No. 11) BamHI site

5'-(GCTCTAGA)-CCG-GCC-GGA-AAC-GG-3' (SEQ ID NO. 12) XbaI site

Figure 5:
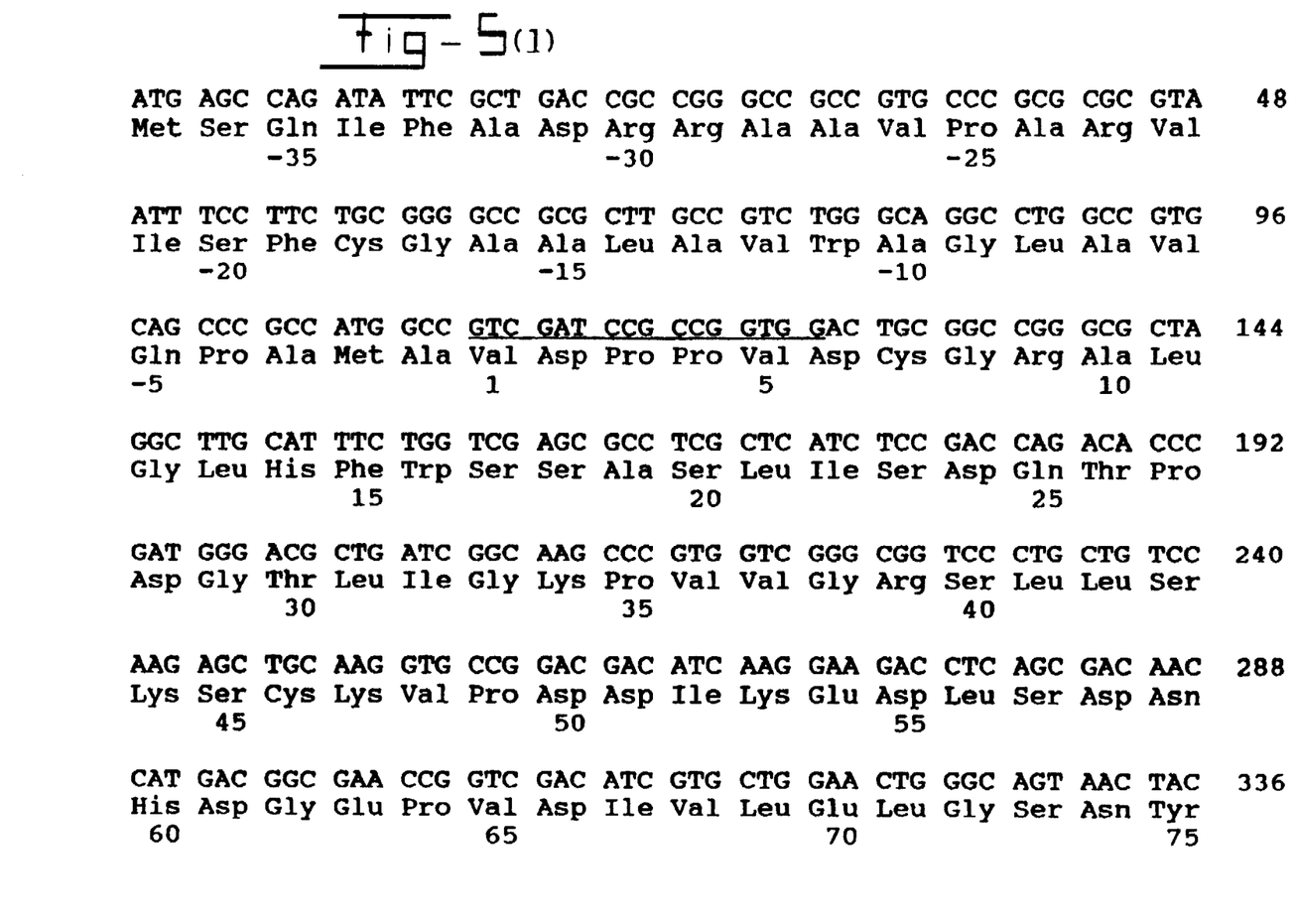
FIG. 5: DNA sequence of fimD, and the deduced amino acid sequence of its product; SEQ ID NOS. 7 and 8. The fimD gene is translated into a precursor of FimD containing a signal peptide of 37 amino acid residues. The signal peptide is removed during or after transport of the precursor across the cytoplasmic membrane. The target DNA used to amplify the fimD sequence with the polymerase chain reaction has been underlined.

The fimD sequences from which the primers were derived have been indicated in FIG. 5 (SEQ ID NO. 7). The bases between brackets indicate extensions which introduce restriction enzyme sites to facilitate cloning.

After amplification, the PCR fragment was purified using agarose gel electrophoresis. The band containing fimD sequences was cut out of the gel, and DNA was purified from the agarose by adsorption to activated glass (Qiaex, DIAGEN GmbH, Dusseldorf) according to the instructions provided by the manufacturer. Subsequently, the fragment was digested with BamHI and XbaI, and inserted into the BamHI/XbaI site of the pUCBM21 polylinker. The resulting plasmid was designated pRIP640.

Plasmid pRIP642 was used as a source of fimD DNA for subsequent constructions. The find gene was excised from pRIP640 with BamHI and HindIII, and purified by agarose gelelectrophoresis as described above. The purified BamHI-HindIII fimD fragment was finally inserted into the BamI/HindIII sites of pMAL-cRI. This construct was designated pRIP642.

Production and Durification of MBP and MBP-FimD fusion protein

E. coli strain BL21 containing pMAL-cRI (for the isolation of MBP) or pRIP642 (for the isolation of the MBP-FimD fusion protein) was grown overnight at 37° C. in Terrific-Broth containing 200 µg/ml ampicillin. The following day, 10 ml was used to inoculate a 1000 ml flask containing 500 ml Terrific Broth supplemented with 200 µg/ml ampicillin, and growth was continued at 37° C. in a shaking water bath until an $OD_{600}$ of 1.0 was reached. At this point, isopropyl-β-D-thiogalactopyranoside (IPTG) was added to a final concentration of 0.5 mM, and incubation was continued for 3 h at 37° C.

Cells were harvested by centrifugation (13000×g, 20 min, 4° C.) and resuspended in buffer A to an $OD_{600}$ of 10. All subsequent steps were performed at 0 to 4° C. in the presence of protease inhibitors (10 mM PMSF, 1 mM 4-amino-benzamidine, 1 nM ε-aminocaproic acid). Forty ml of the cell suspension was frozen, and subsequently thawed after which 25 ml buffer B, 2.5 ml buffer C and milli-Q water to a total volume of 250 ml was added.

Cells were broken by ultrasonication for 4×30 sec with 2 min intervals, using a Branson sonifier at 50% output. Intact cells and large cell fragments were removed by centrifugation (26000×g, 30 min, 4° C.). The supernatant was dialysed against 2 l buffer D. After 16 h, the buffer was refreshed, and dialysis was continued for an additional 2 h. Insoluble material was removed by centrifugation (13000×g, 30 min, 4° C.), and the resulting supernatant was applied to a 5 ml amylose-resin column equilibrated with 10 column volumes of buffer E. From this stage on protease inhibitors were omitted from the solutions. The column was washed with 3 column volumes of buffer E, and subsequently with 5 column volumes of buffer D. Bound protein was eluted with buffer F, and fractions of 0.5 ml were collected. Fractions containing protein, as determined by the Biorad protein assay (Biorad, Hercules, Calif., U.S.A.) were pooled and stored at −20° C. As determined by sodium dodecyl gelelectrophoresis, this procedure resulted in essentially pure (>90%) MBP or MBP-FimD protein (not shown). The yield of the procedure was approximately 12 mg of MBP-FimD per 1 culture.

Terrific Broth:
100 ml Phosphate buffer+900 ml Broth Phosphate buffer: 0.17M $KH_2PO_4$ 0.72M $K_2HPO_4$ Broth: 12 g bacto-trypton, 24 g bacto-yeast extract, 4.0.ml of 87% glycerol. Make up to 900 ml with demi water, autoclave for 20 minutes at 121° C.

Buffer for Durification of MBP(-fusion) proteins

Buffer A
50 mM Tris/HCl (from a 1M stock solution pH 8.0)
5 mM EDTA.
If necessary adjust the pH to 8.0 with NaOH or HCl.

Buffer B
100 mM sodium phosphate
300 mM NaCl
100 mM EDTA
If necessary adjust the pH to 7.0 with NaOH or HCl.

Buffer C
15% Tween 20 v/v in MilliQ water.
Store at room temperature for no longer than one month.

Buffer D
10 mM sodium phosphate
0.5M NaCl
1 mM
1 mM EDTA
If necessary adjust the pH to 7.0 with NaOH or HCl.

Buffer E
Buffer D supplemented with 0.25% Tween 20.

Buffer F
Buffer D supplemented with 10 mM maltose.

Intranasal Protection test

Balb/c mice (3–4 weeks) were immunized (subutaneously) with MBP (25 µg/mouse) or MBP-FimD (50 µg/mouse) in Freund's incomplete adjuvants on day 1 and 14. On day 28 the mice were infected with B. pertussis strain B44 as follows. Mice were lightly anaesthetized with ether, and a drop of 5 µl of the inoculum, containing $10^7$ live B. pertussis, was carefully placed on top of each nostril, and allowed to be inhaled by the animal. Directly after infection, and three and seven days post-infection, mice were killed by intraperitoneal injection of an overdose of a barbiturate (Nembutal®, Sanofi/Algin, Maassluis, The Netherlands). The nasopharynx was sampled by introducing 0.8 ml Verwey medium from the internal side of the animal, and collecting the first ten drops exiting from the nostrils. Subsequently, the lungs and trachea were excised and homogenized in Verwey medium. Viable bacteria in the nasopharynx sample and the homogenates were determined by plating out serial dilutions on Bordet Gengou agar plates. Statistical significance was determined by a the Mann-Whitney Two sample test (one sided).

TABLE 2

Protection conferred by immunization with MBP-FimD in a mouse model

| | | DAY 0 | | | DAY 3 | | | DAY 7 | |
|---|---|---|---|---|---|---|---|---|---|
| | | MEAN | (SD) P | | MEAN | (SD) P | | MEAN | (SD) P |
| | NASO | | | | | | | | |
| C | MBP-FimD | 7,256 | (5,223) C–D ns | | 5,637 | (7,341) C–D ns | | 1,570 | (1,152) C–D ns |
| D | MBP | 13,260 | (13,374) C–E ns | | 4,975 | (6,275) C–E 0.030** | | 3,568 | (5,722) C–E ns |
| E | PBS | 6,533 | (5,807) D–E ns | | 1,982 | (2,856) D–E 0.065* | | 1,792 | (1,891) D–E ns |
| | TRACHEA | | | | | | | | |
| C | MBP-FimD | 1,174 | (1,945) C–D 0.070* | | 10 | (24) C–D 0.016** | | 1,313 | (3,112) C–D 0.079* |
| D | MBP | 1,876 | (1,274) C–E 0.033** | | 64 | (89) C–E 0.016** | | 7,568 | (10,148) C–E 0.017** |
| E | PBS | 2,344 | (1,236) D–E ns | | 69 | (24) D–E ns | | 3,980 | (6,556) D–E ns |
| | LUNG | | | | | | | | |
| C | MBP-FimD | 1,769 | (3,782) C–D 0.029** | | 40 | (126) C–D 0.021** | | 2,840 | (6,368) C–D ns |
| D | MBP | 17,220 | (23,724) C–E 0.007** | | 11,027 | (16,944) C–E 0.100* | | 15,200 | (23,205) C–E 0.037** |
| E | PBS | 14,391 | (16,827) D–E ns | | 15,440 | (27,733) D–E ns | | 8,399 | (11,782) D–E ns |

REMARKS:
P values were calculated according the Mann-Whitney Two-sample test (One sided)
ns not significant (P > 0.100)
*marginally significant
**significant
Abbreviations: SD = Standard Deviation, PBS = Phosphate Buffered Saline, MBP = Maltose binding protein.

---

I claim:

1. A substantially pure protein comprising an amino acid sequence code by SEQ ID NO:7, coding for a minor fimbrial subunit of *Bordetella pertussis* fimbriae (FimD) or immunogenic fragments thereof capable of increasing resistance to colonization by *B. pertussis* strains in trachea and lung tissues, said protein being effective to increase resistance to colonization in trachea and lung tissues by bacteria causative of whooping cough when administered in a vaccine.

2. A vaccine for increasing resistance to colonization in trachea and lung tissues by bacteria causative of whooping cough, comprising an effective amount of a protein as defined in claim 1, in admixture with a pharmaceutically capable excipient.

3. a vaccine for increasing resistance to colonization in animal trachea and lung tissues by *B. bronchiseptica*, comprising an effective amount of a protein as defined in claim 1, in admixture with a veterinary acceptable excipient.

4. A protein consisting of the amino acid sequence of SEQ ID NO:8.

5. A vaccine for increasing resistance to colonization in trachea and lung tissues by bacteria causative of whooping cough, comprising the protein according to claim 4 in admixture with a pharmaceutically acceptable excipient.

6. A substantially pure protein consisting of the amino acid sequence of SEQ ID NO:8, or immunogenic fragments thereof effective to increase resistance to colonization in trachea and lung tissues by bacteria causative of whooping cough when administered in a vaccine.

7. A vaccine for increasing resistance to colonization in trachea and lung tissues by bacteria causative of whooping cough, comprising the protein according to claim 6 in admixture with a pharmaceutically acceptable excipient.

\* \* \* \* \*

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 15 amino acids
        ( B ) TYPE: amino acid
        ( D ) TOPOLOGY: linear     ( i i ) MOLECULE TYPE: peptide     ( v ) FRAGMENT TYPE: N-terminal     ( x i ) SEQUENCE DESCRIPTION: SEQ ID NO:1:

```
Val Gln Pro Pro Val Gln Xaa Gly Arg Ala Ile Gly Leu Gln Phe
 1               5                  10                      15
```

( 2 ) INFORMATION FOR SEQ ID NO:2:

( i ) SEQUENCE CHARACTERISTICS:
        ( A ) LENGTH: 14 amino acids
        ( B ) TYPE: amino acid
        ( D ) TOPOLOGY: linear     ( i i ) MOLECULE TYPE: peptide     ( v ) FRAGMENT TYPE: internal     ( x i ) SEQUENCE DESCRIPTION: SEQ ID NO:2:

```
Lys Ala Gln Tyr Tyr Gln Thr Ser Thr Ser Thr Ser Ala Gly
 1               5                  10
```

( 2 ) INFORMATION FOR SEQ ID NO:3:

( i ) SEQUENCE CHARACTERISTICS:
        ( A ) LENGTH: 21 base pairs
        ( B ) TYPE: nucleic acid (C) STRANDEDNESS: single
(D) TOPOLOGY: linear (ii) MOLECULE TYPE: DNA (genomic)

(iii) HYPOTHETICAL: YES (ix) FEATURE:
(A) NAME/KEY: CDS
(B) LOCATION: 1..21

(ix) FEATURE:
(A) NAME/KEY: mat_peptide
(B) LOCATION: 1..21

(xi) SEQUENCE DESCRIPTION: SEQ ID NO:3:

```
AAG GCC CAG TAC TAC CAG ACC                                              21
Lys Ala Gln Tyr Tyr Gln Thr
 1               5
```

(2) INFORMATION FOR SEQ ID NO:4:

(i) SEQUENCE CHARACTERISTICS:
(A) LENGTH: 7 amino acids
(B) TYPE: amino acid
(D) TOPOLOGY: linear (ii) MOLECULE TYPE: protein (xi) SEQUENCE DESCRIPTION: SEQ ID NO:4:

```
Lys Ala Gln Tyr Tyr Gln Thr
 1               5
```

(2) INFORMATION FOR SEQ ID NO:5:

(i) SEQUENCE CHARACTERISTICS:
(A) LENGTH: 20 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:5:

```
Lys Ile Ala Leu Pro Glu Ala Glu Glu Thr Glu Ser Ala Thr Phe Ser
 1               5                  10                  15

Leu Pro Met Lys
            20
```

(2) INFORMATION FOR SEQ ID NO:6:

(i) SEQUENCE CHARACTERISTICS:
(A) LENGTH: 21 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:6:

```
Lys Thr Gln Thr Gly Val Asp Gly Val Ala Leu Pro Ala Thr Gly Gln
 1               5                  10                  15

Ala Ala Gly Met Ala
            20
```

(2) INFORMATION FOR SEQ ID NO:7:

(i) SEQUENCE CHARACTERISTICS:

(A) LENGTH: 1155 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: mat_peptide
(B) LOCATION: 112..1128

(ix) FEATURE:
(A) NAME/KEY: CDS
(B) LOCATION: 1..1128

(ix) FEATURE:
(A) NAME/KEY: sig_peptide
(B) LOCATION: 1..111

(xi) SEQUENCE DESCRIPTION: SEQ ID NO:7:

| | | | | | | | | | | | | | | | | |
|---|---|---|---|---|---|---|---|---|---|---|---|---|---|---|---|---|
| ATG | AGC | CAG | ATA | TTC | GCT | GAC | CGC | CGG | GCC | GCC | GTG | CCC | GCG | CGC | GTA | 48 |
| Met | Ser | Gln | Ile | Phe | Ala | Asp | Arg | Arg | Ala | Ala | Val | Pro | Ala | Arg | Val | |
| -37 | | -35 | | | | | -30 | | | | | -25 | | | | |
| ATT | TCC | TTC | TGC | GGG | GCC | GCG | CTT | GCC | GTC | TGG | GCA | GGC | CTG | GCC | GTG | 96 |
| Ile | Ser | Phe | Cys | Gly | Ala | Ala | Leu | Ala | Val | Trp | Ala | Gly | Leu | Ala | Val | |
| | -20 | | | | | -15 | | | | | -10 | | | | | |
| CAG | CCC | GCC | ATG | GCC | GTC | GAT | CCG | CCG | GTG | GAC | TGC | GGC | CGG | GCG | CTA | 144 |
| Gln | Pro | Ala | Met | Ala | Val | Asp | Pro | Pro | Val | Asp | Cys | Gly | Arg | Ala | Leu | |
| -5 | | | | 1 | | | | 5 | | | | | | 10 | | |
| GGC | TTG | CAT | TTC | TGG | TCG | AGC | GCC | TCG | CTC | ATC | TCC | GAC | CAG | ACA | CCC | 192 |
| Gly | Leu | His | Phe | Trp | Ser | Ser | Ala | Ser | Leu | Ile | Ser | Asp | Gln | Thr | Pro | |
| | | | 15 | | | | | 20 | | | | | 25 | | | |
| GAT | GGG | ACG | CTG | ATC | GGC | AAG | CCC | GTG | GTC | GGG | CGG | TCC | CTG | CTG | TCC | 240 |
| Asp | Gly | Thr | Leu | Ile | Gly | Lys | Pro | Val | Val | Gly | Arg | Ser | Leu | Leu | Ser | |
| | | 30 | | | | | 35 | | | | | 40 | | | | |
| AAG | AGC | TGC | AAG | GTG | CCG | GAC | GAC | ATC | AAG | GAA | GAC | CTC | AGC | GAC | AAC | 288 |
| Lys | Ser | Cys | Lys | Val | Pro | Asp | Asp | Ile | Lys | Glu | Asp | Leu | Ser | Asp | Asn | |
| | | 45 | | | | | 50 | | | | | 55 | | | | |
| CAT | GAC | GGC | GAA | CCG | GTC | GAC | ATC | GTG | CTG | GAA | CTG | GGC | AGT | AAC | TAC | 336 |
| His | Asp | Gly | Glu | Pro | Val | Asp | Ile | Val | Leu | Glu | Leu | Gly | Ser | Asn | Tyr | |
| 60 | | | | | 65 | | | | | 70 | | | | | 75 | |
| AAG | ATC | CGG | CCG | CAG | TCC | TAT | GGC | CAT | CCG | GGC | ATC | GTG | GTC | GAC | TTG | 384 |
| Lys | Ile | Arg | Pro | Gln | Ser | Tyr | Gly | His | Pro | Gly | Ile | Val | Val | Asp | Leu | |
| | | | | 80 | | | | | 85 | | | | | 90 | | |
| CCG | TTC | GGC | TCC | ACG | GAG | GAG | ACC | GGC | ATC | GCC | ATC | TAT | ATC | GAT | TTC | 432 |
| Pro | Phe | Gly | Ser | Thr | Glu | Glu | Thr | Gly | Ile | Ala | Ile | Tyr | Ile | Asp | Phe | |
| | | | 95 | | | | | 100 | | | | | 105 | | | |
| GGC | AGT | TCG | CCG | ATG | CAG | AAG | GTC | GGC | GAA | CGG | CAG | TGG | CTG | TAT | CCC | 480 |
| Gly | Ser | Ser | Pro | Met | Gln | Lys | Val | Gly | Glu | Arg | Gln | Trp | Leu | Tyr | Pro | |
| | | 110 | | | | | 115 | | | | | 120 | | | | |
| CAG | AAA | GGC | GAA | GTG | CTT | TTC | GAC | GTG | CTC | ACC | ATC | AAC | GGC | GAC | AAC | 528 |
| Gln | Lys | Gly | Glu | Val | Leu | Phe | Asp | Val | Leu | Thr | Ile | Asn | Gly | Asp | Asn | |
| | 125 | | | | | 130 | | | | | 135 | | | | | |
| GCG | GAG | GTT | CGC | TAT | CAG | GCG | ATC | AAG | GTC | GGG | CCA | CTC | AAG | CGG | CCG | 576 |
| Ala | Glu | Val | Arg | Tyr | Gln | Ala | Ile | Lys | Val | Gly | Pro | Leu | Lys | Arg | Pro | |
| 140 | | | | | 145 | | | | | 150 | | | | | 155 | |
| CGC | AAG | CTG | GTG | CTG | TCG | CAG | TTT | CCG | AAC | CTG | TTC | ACC | TAC | AAG | TGG | 624 |
| Arg | Lys | Leu | Val | Leu | Ser | Gln | Phe | Pro | Asn | Leu | Phe | Thr | Tyr | Lys | Trp | |
| | | | | 160 | | | | | 165 | | | | | 170 | | |
| GTT | TTC | ATG | CGC | GGG | ACC | AGC | CAG | GAG | CGC | GTG | CTG | GCG | CAG | GGG | ACC | 672 |
| Val | Phe | Met | Arg | Gly | Thr | Ser | Gln | Glu | Arg | Val | Leu | Ala | Gln | Gly | Thr | |
| | | | 175 | | | | | 180 | | | | | 185 | | | |
| ATC | GAC | ACC | GAC | GTC | GCC | ACC | AGC | ACC | ATC | GAC | CTG | AAA | ACC | TGC | CGC | 720 |
| Ile | Asp | Thr | Asp | Val | Ala | Thr | Ser | Thr | Ile | Asp | Leu | Lys | Thr | Cys | Arg | |
| | | 190 | | | | | 195 | | | | | 200 | | | | |

| | | | | | | | | | | | | | | | | |
|---|---|---|---|---|---|---|---|---|---|---|---|---|---|---|---|---|
| TAT | ACC | TCG | CAG | ACG | GTC | AGC | CTG | CCC | ATC | ATC | CAG | CGT | TCC | GCG | TTG | 768 |
| Tyr | Thr | Ser | Gln | Thr | Val | Ser | Leu | Pro | Ile | Ile | Gln | Arg | Ser | Ala | Leu | |
| | 205 | | | | 210 | | | | | | 215 | | | | | |
| ACC | GGC | GTC | GGT | ACG | ACC | CTG | GGG | ATG | ACC | GAT | TTC | CAG | ATG | CCG | TTC | 816 |
| Thr | Gly | Val | Gly | Thr | Thr | Leu | Gly | Met | Thr | Asp | Phe | Gln | Met | Pro | Phe | |
| 220 | | | | | 225 | | | | 230 | | | | | | 235 | |
| TGG | TGC | TAT | GGC | TGG | CCA | AAG | GTG | TCG | GTG | TAC | ATG | AGC | GCG | ACG | AAG | 864 |
| Trp | Cys | Tyr | Gly | Trp | Pro | Lys | Val | Ser | Val | Tyr | Met | Ser | Ala | Thr | Lys | |
| | | | 240 | | | | | 245 | | | | | | 250 | | |
| ACG | CAG | ACC | GGC | GTA | GAC | GGC | GTG | GCG | TTG | CCG | GCG | ACC | GGC | CAG | GCG | 912 |
| Thr | Gln | Thr | Gly | Val | Asp | Gly | Val | Ala | Leu | Pro | Ala | Thr | Gly | Gln | Ala | |
| | | | 255 | | | | | 260 | | | | | 265 | | | |
| GCC | GGC | ATG | GCC | AGC | GGC | GTA | GGC | GTC | CAG | TTG | ATC | AAC | GGC | AAG | ACG | 960 |
| Ala | Gly | Met | Ala | Ser | Gly | Val | Gly | Val | Gln | Leu | Ile | Asn | Gly | Lys | Thr | |
| | | 270 | | | | | 275 | | | | | 280 | | | | |
| CAG | CAG | CCG | GTC | AAG | CTG | GGC | CTG | CAG | GGC | AAG | ATC | GCC | TTG | CCC | GAG | 1008 |
| Gln | Gln | Pro | Val | Lys | Leu | Gly | Leu | Gln | Gly | Lys | Ile | Ala | Leu | Pro | Glu | |
| | 285 | | | | | 290 | | | | | 295 | | | | | |
| GCG | CAG | CAG | ACT | GAG | TCG | GCG | ACG | TTC | TCG | CTG | CCC | ATG | AAG | GCG | CAG | 1056 |
| Ala | Gln | Gln | Thr | Glu | Ser | Ala | Thr | Phe | Ser | Leu | Pro | Met | Lys | Ala | Gln | |
| 300 | | | | | 305 | | | | | 310 | | | | | 315 | |
| TAC | TAC | CAG | ACC | TCC | ACT | TCA | ACC | TCG | GCG | GGC | AAG | CTG | TCC | GTC | ACC | 1104 |
| Tyr | Tyr | Gln | Thr | Ser | Thr | Ser | Thr | Ser | Ala | Gly | Lys | Leu | Ser | Val | Thr | |
| | | | 320 | | | | | 325 | | | | | 330 | | | |
| TAC | GCC | GTG | ACC | TTG | AAC | TAT | GAC | TGACGCAACG | | AACCGTTTCC | | GGCCGGG | | | | 1155 |
| Tyr | Ala | Val | Thr | Leu | Asn | Tyr | Asp | | | | | | | | | |
| | | 335 | | | | | | | | | | | | | | |

( 2 ) INFORMATION FOR SEQ ID NO:8:

( i ) SEQUENCE CHARACTERISTICS:
        ( A ) LENGTH: 376 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:8:

| | | | | | | | | | | | | | |
|---|---|---|---|---|---|---|---|---|---|---|---|---|---|
| Met | Ser | Gln | Ile | Phe | Ala | Asp | Arg | Arg | Ala | Ala | Val | Pro | Ala | Arg | Val |
| -37 | | -35 | | | | | -30 | | | | | -25 | | | |
| Ile | Ser | Phe | Cys | Gly | Ala | Ala | Leu | Ala | Val | Trp | Ala | Gly | Leu | Ala | Val |
| | -20 | | | | | -15 | | | | | -10 | | | | |
| Gln | Pro | Ala | Met | Ala | Val | Asp | Pro | Pro | Val | Asp | Cys | Gly | Arg | Ala | Leu |
| -5 | | | | 1 | | | | 5 | | | | | | 10 | |
| Gly | Leu | His | Phe | Trp | Ser | Ser | Ala | Ser | Leu | Ile | Ser | Asp | Gln | Thr | Pro |
| | | | 15 | | | | | 20 | | | | | 25 | | |
| Asp | Gly | Thr | Leu | Ile | Gly | Lys | Pro | Val | Val | Gly | Arg | Ser | Leu | Leu | Ser |
| | | 30 | | | | | 35 | | | | | 40 | | | |
| Lys | Ser | Cys | Lys | Val | Pro | Asp | Asp | Ile | Lys | Glu | Asp | Leu | Ser | Asp | Asn |
| | 45 | | | | | 50 | | | | | 55 | | | | |
| His | Asp | Gly | Glu | Pro | Val | Asp | Ile | Val | Leu | Glu | Leu | Gly | Ser | Asn | Tyr |
| 60 | | | | | 65 | | | | | 70 | | | | | 75 |
| Lys | Ile | Arg | Pro | Gln | Ser | Tyr | Gly | His | Pro | Gly | Ile | Val | Val | Asp | Leu |
| | | | | 80 | | | | | 85 | | | | | 90 | |
| Pro | Phe | Gly | Ser | Thr | Glu | Glu | Thr | Gly | Ile | Ala | Ile | Tyr | Ile | Asp | Phe |
| | | | | 95 | | | | | 100 | | | | | 105 | |
| Gly | Ser | Ser | Pro | Met | Gln | Lys | Val | Gly | Glu | Arg | Gln | Trp | Leu | Tyr | Pro |
| | | | 110 | | | | | 115 | | | | | 120 | | |
| Gln | Lys | Gly | Glu | Val | Leu | Phe | Asp | Val | Leu | Thr | Ile | Asn | Gly | Asp | Asn |

```
             125                           130                           135
Ala  Glu  Val  Arg  Tyr  Gln  Ala  Ile  Lys  Val  Gly  Pro  Leu  Lys  Arg  Pro
140                      145                      150                      155

Arg  Lys  Leu  Val  Leu  Ser  Gln  Phe  Pro  Asn  Leu  Phe  Thr  Tyr  Lys  Trp
                    160                      165                     170

Val  Phe  Met  Arg  Gly  Thr  Ser  Gln  Glu  Arg  Val  Leu  Ala  Gln  Gly  Thr
               175                      180                          185

Ile  Asp  Thr  Asp  Val  Ala  Thr  Ser  Thr  Ile  Asp  Leu  Lys  Thr  Cys  Arg
          190                     195                         200

Tyr  Thr  Ser  Gln  Thr  Val  Ser  Leu  Pro  Ile  Ile  Gln  Arg  Ser  Ala  Leu
     205                     210                     215

Thr  Gly  Val  Gly  Thr  Thr  Leu  Gly  Met  Thr  Asp  Phe  Gln  Met  Pro  Phe
220                      225                     230                          235

Trp  Cys  Tyr  Gly  Trp  Pro  Lys  Val  Ser  Val  Tyr  Met  Ser  Ala  Thr  Lys
               240                          245                         250

Thr  Gln  Thr  Gly  Val  Asp  Gly  Val  Ala  Leu  Pro  Ala  Thr  Gly  Gln  Ala
               255                     260                          265

Ala  Gly  Met  Ala  Ser  Gly  Val  Gly  Val  Gln  Leu  Ile  Asn  Gly  Lys  Thr
          270                      275                     280

Gln  Gln  Pro  Val  Lys  Leu  Gly  Leu  Gln  Gly  Lys  Ile  Ala  Leu  Pro  Glu
     285                      290                          295

Ala  Gln  Gln  Thr  Glu  Ser  Ala  Thr  Phe  Ser  Leu  Pro  Met  Lys  Ala  Gln
300                     305                      310                          315

Tyr  Tyr  Gln  Thr  Ser  Thr  Ser  Thr  Ser  Ala  Gly  Lys  Leu  Ser  Val  Thr
               320                     325                          330

Tyr  Ala  Val  Thr  Leu  Asn  Tyr  Asp
               335
```

( 2 ) INFORMATION FOR SEQ ID NO:9:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear     ( i i ) MOLECULE TYPE: DNA (genomic)

( i x ) FEATURE:
        ( A ) NAME/KEY: CDS
        ( B ) LOCATION: 1..48

( i x ) FEATURE:
        ( A ) NAME/KEY: mat_peptide
        ( B ) LOCATION: 1..48

( x i ) SEQUENCE DESCRIPTION: SEQ ID NO:9:

```
ATC  GAG  GGA  AGG  ATT  TCA  GAA  TTC  GGA  TCC  GTC  CAT  CCG  TAT  GAC  TAG   48
Ile  Glu  Gly  Arg  Ile  Ser  Glu  Phe  Gly  Ser  Val  His  Pro  Tyr  Asp
 1                    5                        10                      15
```

( 2 ) INFORMATION FOR SEQ ID NO:10:

( i ) SEQUENCE CHARACTERISTICS:
        ( A ) LENGTH: 15 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:10:

```
Ile  Glu  Gly  Arg  Ile  Ser  Glu  Phe  Gly  Ser  Val  His  Pro  Tyr  Asp
 1                    5                        10                      15
```

(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear     (ii) MOLECULE TYPE: DNA (genomic)

(iii) HYPOTHETICAL: YES

(xi) SEQUENCE DESCRIPTION: SEQ ID NO:11:

```
ATGGATCCGT CGATCCGCCG GTGG                                    24
```

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear     (ii) MOLECULE TYPE: DNA (genomic)

(iii) HYPOTHETICAL: YES

(xi) SEQUENCE DESCRIPTION: SEQ ID NO:12:

```
GCTCTAGACC GGCCGGAAAC GG                                      22
```